US00PP20092P2

(12) United States Plant Patent
Kanaya

(10) Patent No.: US PP20,092 P2
(45) Date of Patent: Jun. 9, 2009

(54) ***CALIBRACHOA* PLANT NAMED 'SUNBEL KOPACHIPI'**

(50) Latin Name: ***Calibrachoa* sp.**
Varietal Denomination: Sunbel Kopachipi

(75) Inventor: Takeshi Kanaya, Shiga (JP)

(73) Assignee: Suntory Flowers Limited, Tokyo (JP)

( * ) Notice: Subject to any disclaimer, the term of this patent is extended or adjusted under 35 U.S.C. 154(b) by 0 days.

(21) Appl. No.: 12/077,208

(22) Filed: Mar. 17, 2008

(51) Int. Cl.
*A01H 5/00* (2006.01)

(52) U.S. Cl. ..... Plt./413
(58) Field of Classification Search ..... Plt./263, Plt./413
See application file for complete search history.

*Primary Examiner*—S. B. McCormick Ewoldt
(74) *Attorney, Agent, or Firm*—C. A. Whealy

(57) ABSTRACT

A new and distinct cultivar of *Calibrachoa* plant named 'Sunbel Kopachipi', characterized by its compact and mounding plant habit; vigorous growth habit; freely branching habit; early and freely flowering habit; long flowering period; and intense red purple-colored flowers.

1 Drawing Sheet

Botanical designation: *Calibrachoa* sp.
Cultivar denomination: 'Sunbel Kopachipi'.

BACKGROUND OF THE INVENTION

The present invention relates to a new and distinct cultivar of *Calibrachoa,* botanically known as *Calibrachoa* sp. and hereinafter referred to by the name 'Sunbel Kopachipi'.

The new *Calibrachoa* is a product of a planned breeding program conducted by the Inventor in Higashiomi, Shiga, Japan. The objective of the breeding program is to develop new uniform *Calibrachoa* cultivars with attractive and unique flower coloration.

The new *Calibrachoa* originated from a cross-pollination conducted by the Inventor in Higashiomi, Shiga, Japan in April, 2003 of a proprietary selection of *Calibrachoa* sp. identified as code number C58, not patented, as the female, or seed, parent with a proprietary selection of *Calibrachoa* sp. identified as code number GF1, not patented, as the male, or pollen, parent. The cultivar Sunbel Kopachipi was discovered and selected by the Inventor as a flowering plant from within the progeny of the stated cross-pollination in a controlled greenhouse environment in Higashiomi, Shiga, Japan.

Asexual reproduction of the new *Calibrachoa* by vegetative cuttings in a controlled environment in Higashiomi, Shiga, Japan since September, 2005, has shown that the unique features of this new *Calibrachoa* are stable and reproduced true to type in successive generations.

SUMMARY OF THE INVENTION

The cultivar Sunbel Kopachipi has not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'Sunbel Kopachipi'. These characteristics in combination distinguish 'Sunbel Kopachipi' as a new and distinct cultivar of *Calibrachoa:*

1. Compact and mounding plant habit.
2. Vigorous growth habit.
3. Freely branching habit.
4. Early and freely flowering habit.
5. Long flowering period.
6. Intense red purple-colored flowers.

Plants of the new *Calibrachoa* can be compared to plants of the female parent selection. Plants of the new *Calibrachoa* differ from plants of the female parent selection in the following characteristics:

1. Plants of the new *Calibrachoa* are not as broad as plants of the female parent selection.
2. Plants of the new *Calibrachoa* have larger flowers than plants of the female parent selection.

Plants of the new *Calibrachoa* can be compared to plants of the male parent selection. Plants of the new *Calibrachoa* differ primarily from plants of the male parent selection in flower color as plants of the male parent selection have dull red purple-colored flowers.

Plants of the new *Calibrachoa* can also be compared to plants of the cultivar Sunbelochipi, disclosed in U.S. Plant Pat. No. 10,355. In side-by-side comparisons conducted in Higashiomi, Shiga, Japan, plants of the new *Calibrachoa* and the cultivar Sunbelochipi differed in the following characteristics:

1. Plants of the new *Calibrachoa* were more compact and mounding than plants of the cultivar Sunbelochipi.
2. Plants of the new *Calibrachoa* had shorter internodes than plants of the cultivar Sunbelochipi.
3. Plants of the new *Calibrachoa* were more freely branching than plants of the cultivar Sunbelochipi.
4. Plants of the new *Calibrachoa* were more freely flowering than plants of the cultivar Sunbelochipi.
5. Plants of the new *Calibrachoa* had larger flowers than plants of the cultivar Sunbelochipi.
6. Plants of the new *Calibrachoa* and the cultivar Sunbelochipi differed in flower color as plants of the cultivar Sunbelochipi had light red purple-colored flowers.

BRIEF DESCRIPTION OF THE PHOTOGRAPHS

The accompanying colored photographs illustrate the overall appearance of the new *Calibrachoa,* showing the colors as true as it is reasonably possible to obtain in colored reproductions of this type. Colors in the photographs may differ slightly from the color values cited in the detailed botanical description which accurately describe the colors of the new *Calibrachoa.*

The photograph at the top of the sheet comprises a side perspective view of a typical flowering plant of 'Sunbel Kopachipi' grown in a container.

The photograph at the bottom of the sheet comprises a close-up view of typical flowers of 'Sunbel Kopachipi'.

DETAILED BOTANICAL DESCRIPTION

The aforementioned photographs and following observations, measurements and values describe plants grown in Higashiomi, Shiga, Japan, under commercial practice during the late spring and summer in a polyethylene-covered greenhouse. During the production of the plants, day temperatures averaged 23° C. and night temperatures averaged 13° C. Plants had been growing for about four months when the photographs and description were taken. In the following description, color references are made to The Royal Horticultural Society Colour Chart, 2001 Edition, except where general terms of ordinary dictionary significance are used.

Botanical classification: *Calibrachoa* sp. cultivar Sunbel Kopachipi.

Parentage:

*Female, or seed, parent.*—Proprietary selection of *Calibrachoa* sp. identified as code number C58, not patented.

*Male, or pollen, parent.*—Proprietary selection of *Calibrachoa* sp. identified as code number GF1, not patented.

Propagation:

*Type.*—By vegetative cuttings.

*Time to initiate roots.*—About one week at 20° C. to 25° C.

*Time to produce a rooted young plant.*—About three weeks at 20° C. to 25° C.

*Root description.*—Fine, fibrous, fleshy; light brown in color.

*Rooting habit.*—Freely branching.

Plant description:

*Plant and growth habit.*—Compact and mounding plant habit; mounding. Freely branching with lateral branches potentially forming at every node; pinching enhances lateral branch development. Vigorous growth habit.

*Plant height.*—About 14 cm.

*Plant diameter.*—About 31 cm.

Lateral branch description:

*Length.*—About 17 cm.

*Diameter.*—About 1.5 mm.

*Internode length.*—About 6 mm.

*Strength.*—Strong.

*Aspect.*—Upright to outward.

*Texture.*—Pubescent.

*Color.*—Close to 144B.

Foliage description:

*Arrangement.*—Alternate, simple.

*Length.*—About 3.3 cm.

*Width.*—About 1.2 cm.

*Shape.*—Obovate.

*Apex.*—Broadly acute.

*Base.*—Cuneate.

*Margin.*—Entire.

*Texture, upper and lower surfaces.*—Pubescent.

*Venation pattern.*—Pinnate; reticulate.

*Color.*—Developing and fully expanded foliage, upper surface: Close to 137C; venation, close to 145A. Developing and fully expanded foliage, lower surface: Close to 143C; venation, close to 145A.

*Petiole.*—Length: About 2.7 mm. Diameter: About 1.7 mm. Texture, upper and lower surfaces: Sparsely pubescent. Color, upper and lower surfaces: Close to 145A.

Flower description:

*Flower arrangement and habit.*—Single salverform flowers arising from upper leaf axils. Freely flowering habit with usually about two open flowers per lateral branch. Flowers face upright or outwardly. Flowers not fragrant.

*Natural flowering season.*—Plants of the new *Calibrachoa* initiate and develop flowers about three to four weeks after planting. Long flowering period; flowering commences naturally during the spring and plants flower continuously throughout the summer until late autumn in Japan.

*Flower longevity.*—Individual flowers last about seven to ten days on the plant. Flowers not persistent.

*Flower diameter.*—About 3.5 cm.

*Flower length (depth).*—About 3.1 cm.

*Throat diameter.*—About 7.4 mm.

*Tube length.*—About 1.8 cm.

*Tube diameter.*—About 1.9 mm.

*Flower bud.*—Shape: Cylindrical. Length: About 2 cm. Diameter: About 5.5 mm. Color: Close to N77B.

*Corolla.*—Arrangement: Five petals fused at the base and opening into a flared trumpet. Petal length from throat: About 1.6 cm. Petal width: About 1.6 cm. Petal shape: Spatulate. Petal apex: Rounded with truncate tendencies. Petal margin: Entire. Petal texture, upper and lower surfaces: Smooth, glabrous; velvety. Throat texture: Smooth, glabrous. Tube texture: Smooth, glabrous. Color: Petal, when opening, upper surface: Close to 61B; venation, close to N187A. Petal, when opening, lower surface: Close to 60D; venation, 200A. Petal, fully opened, upper surface: Close to 61B; towards the throat, close to 60A; venation, close to N187A; color becoming closer to 61C with development. Petal, fully opened, lower surface: Close to 60D; venation, close to 200A. Throat: Close to 12A; venation, close to 166A. Tube: Close to 10B; venation, close to 187A.

*Calyx.*—Arrangement: One star-shaped calyx tube with five sepals fused at the base per flower. Sepal length: About 7.7 mm to 12.6 mm. Sepal width: About 3.6 mm. Sepal shape: Lanceolate. Sepal apex: Broadly acute. Sepal margin: Entire. Sepal texture, upper and lower surfaces: Pubescent. Color, immature and mature, upper surface: Close to 138A. Color, immature and mature, lower surface: Close to 138A.

*Peduncles.*—Length: About 1 cm. Diameter: About 0.9 mm. Angle: Upright to outward. Strength: Strong. Texture: Smooth, glabrous. Color: Close to 144A.

*Reproductive organs.*—Stamens: Quantity/arrangement: Five per flower. Stamen length: About 1 cm to 1.3 cm. Anther shape: Ellipsoidal. Anther size: About 1.5 mm by 1.8 mm. Anther color: Close to 3A. Pollen amount: Moderate. Pollen color: Close to 8C. Pistils: Quantity: One per flower. Pistil length: About 1.2 cm. Style color: Close to 145C. Stigma shape: Transversely ellipsoidal. Stigma color: Close to 145A. Ovary color: Close to 144B. Seed/fruit: Seed and fruit development have not been observed on plants of the new *Calibrachoa.*

Temperature tolerance: Plants of the new *Calibrachoa* have been observed to tolerate temperatures from about 5° C. to about 35° C.

Pathogen/pest resistance: Plants of the new *Calibrachoa* have not been observed to be resistant to pests and pathogens common to *Calibrachoa.*

It is claimed:

1. A new and distinct *Calibrachoa* plant named 'Sunbel Kopachipi' as illustrated and described.

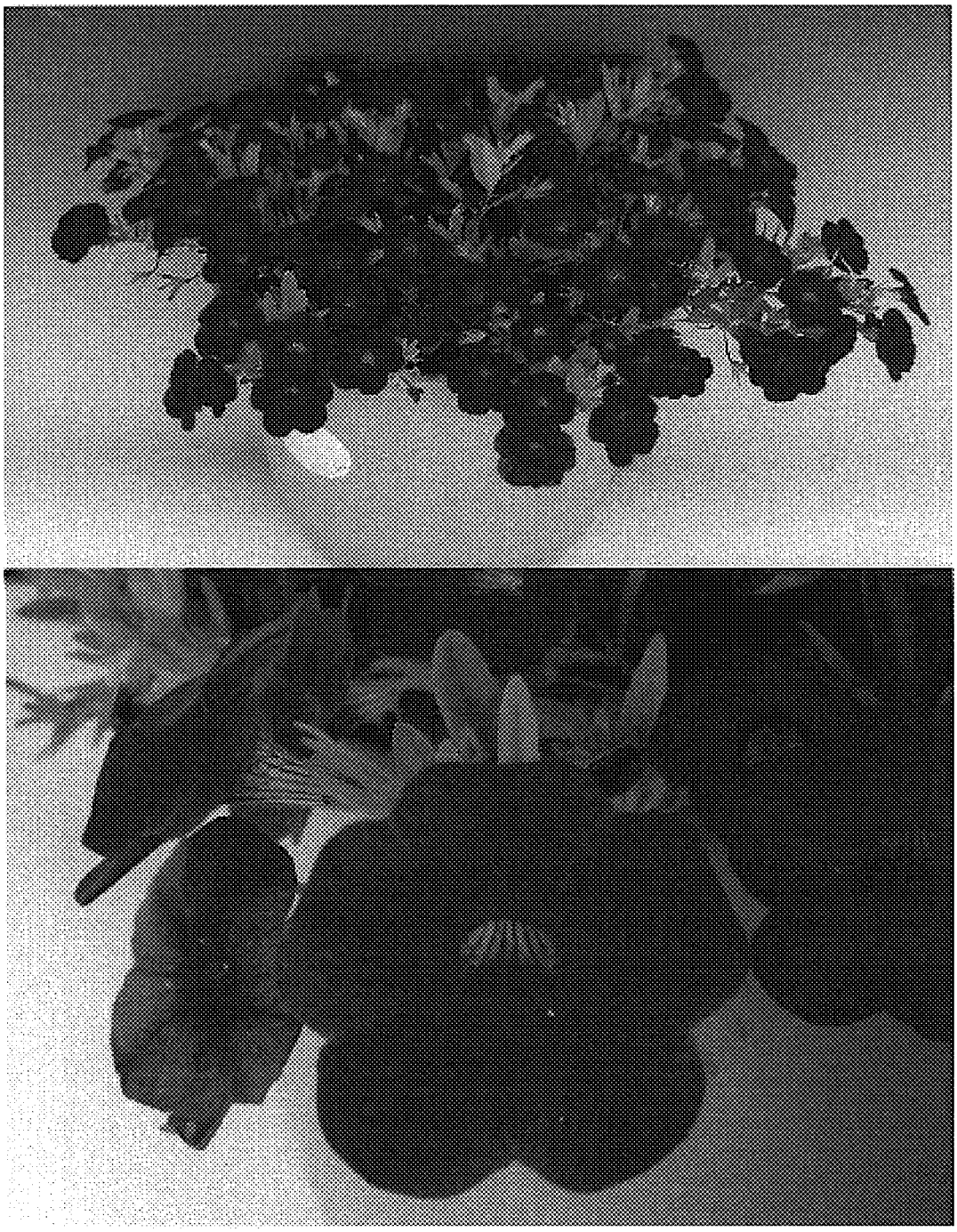

* * * * *